US008666761B2

(12) United States Patent
Fabius et al.

(10) Patent No.: US 8,666,761 B2
(45) Date of Patent: Mar. 4, 2014

(54) SYSTEM AND METHOD FOR AN INTEGRATED DISEASE MANAGEMENT SYSTEM

(75) Inventors: Raymond Fabius, Newtown Square, PA (US); Patricia Kirkpatrick, Spring Hill, TN (US); Sharon G. Frazee, Lebanon, TN (US)

(73) Assignee: Walgreen Co., Deerfield, IL (US)

( * ) Notice: Subject to any disclaimer, the term of this patent is extended or adjusted under 35 U.S.C. 154(b) by 1964 days.

(21) Appl. No.: 11/555,554

(22) Filed: Nov. 1, 2006

(65) Prior Publication Data

US 2008/0103814 A1 May 1, 2008

(51) Int. Cl.
*G06Q 10/00* (2012.01)
*G06Q 50/00* (2012.01)

(52) U.S. Cl.
USPC .............................................................. 705/2

(58) Field of Classification Search
USPC .......................................................... 705/2–3
See application file for complete search history.

(56) References Cited

U.S. PATENT DOCUMENTS

| 5,940,802 | A | 8/1999 | Hildebrand et al. | 705/3 |
|---|---|---|---|---|
| 6,234,964 | B1 | 5/2001 | Iliff | 600/300 |
| 6,470,320 | B1 | 10/2002 | Hildebrand et al. | 705/3 |
| 6,770,029 | B2 | 8/2004 | Iliff | 600/300 |
| 6,936,007 | B2 | 8/2005 | Quy | 600/300 |
| 2002/0194022 | A1* | 12/2002 | Comite | 705/2 |

OTHER PUBLICATIONS

Piatt et al., "Translating the Chronic Care Model Into the Community," Diabetes Care, vol. 29, No. 4, Apr. 2006, pp. 811-817.
MacKinnon et al., "Disease management program for asthma: Baseline assessment of resource use," Am J Health-Syst Pharm, vol. 53, Mar. 1, 1996, pp. 535-541.
Celeste-Harris et al., "Educating medical Office Staff: Enhancing Diabetes Care in Primary Care Office," Diabetes Spectrum, vol. 19, No. 2, 2006, pp. 84-89.

* cited by examiner

*Primary Examiner* — Minnah Seoh
(74) *Attorney, Agent, or Firm* — Francis C. Kowalik; Marshall, Gerstein & Borun LLP; Randall G. Rueth

(57) ABSTRACT

An apparatus, method, and system for the design, administration and implementation of integrated disease management. The integrated disease management ("IDM") system maximizes contact and enrollment rates of traditional remote disease management alone. This is accomplished through the creation of a system that combines telephonic-delivered disease management (i.e. traditional disease management) with work-site based health center clinician ("trusted clinician"). The IDM program is characterized by the involvement of a trusted clinician who actively participates in the disease management program by being involved in the stratification process, the contact step and the process of creating and updating the patient's individualized care plan. Therefore, the IDM program also allows the clinician to be involved in both contact and enrollment phases of the program. The IDM program further increases the efficiency of the disease management program by allowing employers to realize higher returns on their investment into such programs.

19 Claims, 6 Drawing Sheets

IDM PHARMACY REFERRAL PROCESS

FIGURE 4

SAMPLE CARE PLAN

Health-e-Coordinator Activity Screen:

Test. Enrollment | 123-456-7890 | F | 40 y | High
Member Activities                                                                 BearLimited | Case DM S: All

| Due Date | Date Complete | Assigned To | Completed | Activity | Status | Select |
|---|---|---|---|---|---|---|
| 9/13/2006 | | Doe, Jenny | | Advise member to take their zone report and journal to next physician visit. | Planned | View |
| 9/13/2006 | | Doe, Jenny | | Confirm member had follow up visit with physician after completion of oral steroid course. If not, re-advise member to do so. | Planned | View |
| 10/2/2006 | | Doe, Jenny | | Hypertension routine follow up call | Planned | View |
| 10/2/2006 | | Doe, Jenny | | Remind member to get flu vaccination. | Planned | View |
| 9/7/2007 | | Doe, Jenny | | High Avoidable General Assessment | Planned | View |
| | 9/8/2006 | Miltenberger | | Fulfillment: Send Patient Pathway for Hypertension (H-AP) | Complete | View |
| | 9/8/2006 | Miltenberger | | Fulfillment: Send Nutrition Eating For Life (W-2) | Complete | View |
| | 9/8/2006 | Miltenberger | | Fulfillment: Send My Food Diary (W-3) | Complete | View |
| | 9/8/2006 | Miltenberger | | Fulfillment: Send My Blood Pressure Log (H-5) | Complete | View |
| | 9/8/2006 | Miltenberger | | Fulfillment: Send Hypertension Website Sheet (H-4) | Complete | View |
| | 9/8/2006 | Miltenberger | | Fulfillment: Send High Blood Pressure – Self Care Guide (H-3) | Complete | View |
| | 9/8/2006 | Miltenberger | | Follow up call for medication compliance. | Complete | View |
| | 9/8/2006 | Miltenberger | | Advise member to use conservative treatment such as alternating ice/heat packs, use of proper upper body mechanics, avoiding excessive sitting and prolonged bed rest. | Complete | View |
| | 9/8/2006 | Miltenberger | | Advise member to contact physician's office if they have not reviewed nose bleeds, headache, or dizziness symptoms at their most recent office visit. | Complete | View |
| | 9/8/2006 | Miltenberger | | Advise member to contact physician's office if they have not reviewed chest pain, angina, abdominal pain, or shortness of breath symptoms at their most recent office visit. | Complete | View |

Clinical Notes in Health-e-Coordinator:

Test. Enrollment | 123-456-7890 | F | 40 y | High
View Note                                                                         BearLimited | Case DM

| | |
|---|---|
| Date | 9/8/2006 17:00 |
| Note Type | Health Center Note |
| Contact | Member |
| Entered By | Miltenberger, Sheryl |
| Subject | Clinical Note - Initial |
| Action | Goals and Interventions Established |
| Detail | Spoke with patient this date. Confirmed physician appt was last week, saw Dr. Peco for back and leg pain, received referral to orthopedic physician. Was given a muscle relaxer but stopped it's use as it gave her stomach pain, stated she told Dr. Peco. |
| | Last blood pressure was 156/90. No recent labs, has an appointment on 9/11/06 at the HC to have labs drawn, then a follow-up visit with Dr. Peco on 9/17/06 to review results. States has been feeling fairly well. Dr. Peco did check feet at last visit, no dental care necessary, has dentures, reminded should still have mouth examined routinely especially for any denture pressure sores. Has cataracts and has routine visits with eye specialist. Asked what areas she wanted to improve and spoke about reducing blood pressure. Patient agreed to work on setting goals for diet, will review materials previously sent and determine one item to change in diet. Patient stated she would have labs drawn as scheduled and this writer explained we would get the results and review them and set goals for dietary changes. Patient does not follow any specific diet at this time. |
| | Goal: lower blood pressure by 10 points |
| | Intervention: review nutrition information in materials sent by this date. |
| | Intervention: determine one thing she can change to improve compliancy with dietary needs by 10/2/06. |
| | Intervention: show for lab draws on 9/11/06 and review with Nurse Coach on 10/2/06.sm |

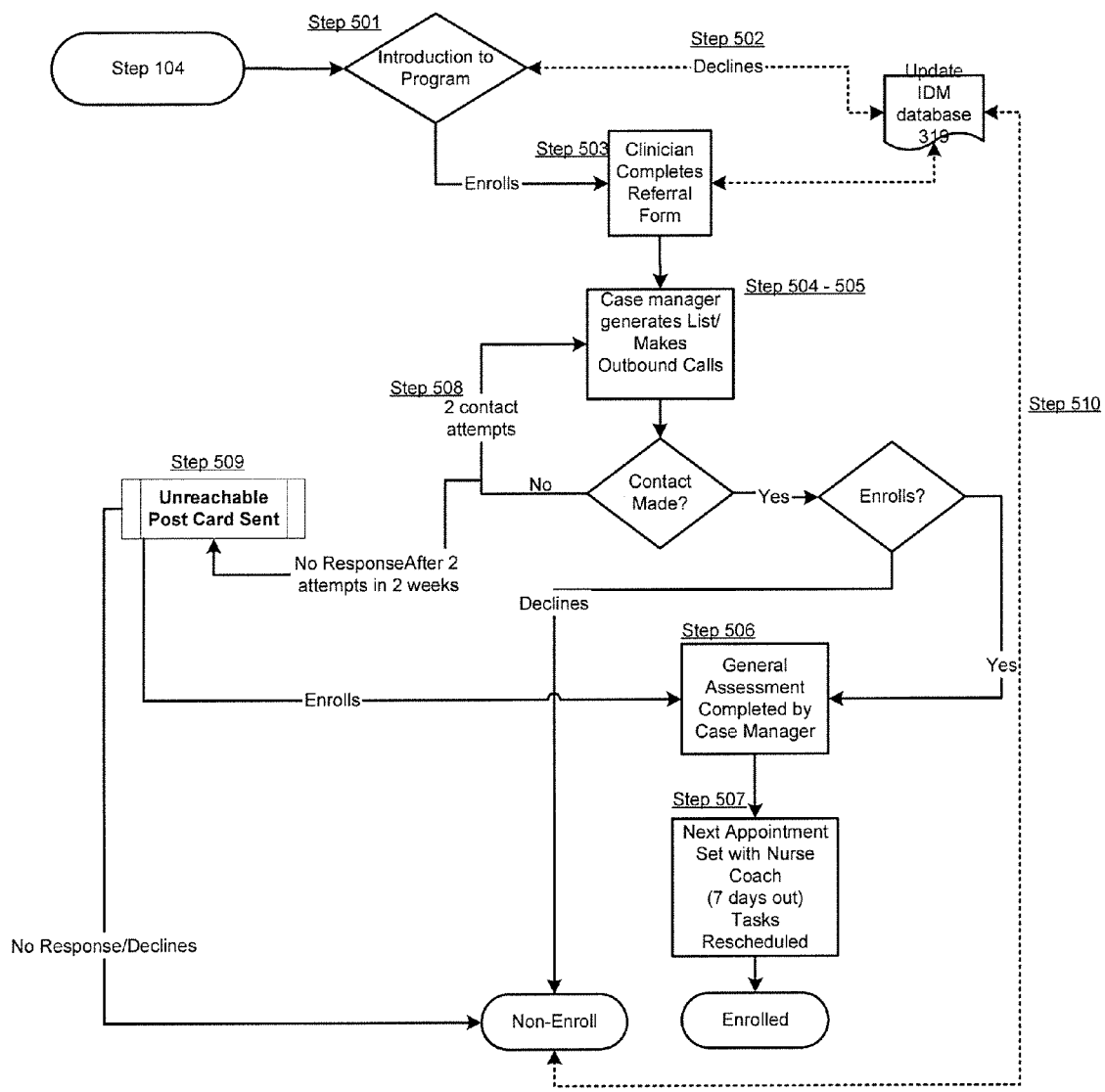
FIGURE 5 - Pre-Enrollment and Enrollment Flow Chart

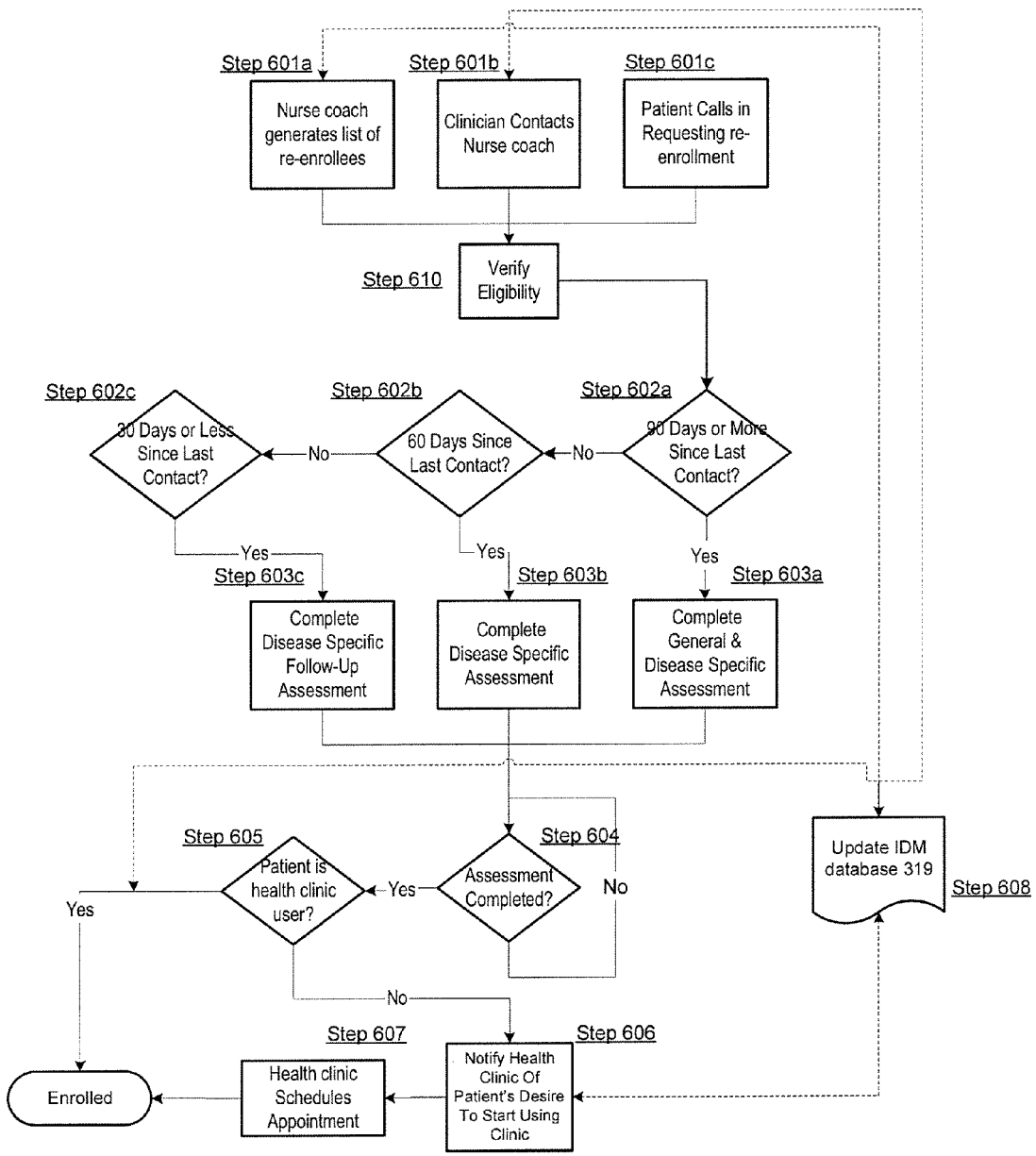
FIGURE 6 - Re-Enrollment Flow Chart

SYSTEM AND METHOD FOR AN INTEGRATED DISEASE MANAGEMENT SYSTEM

FIELD

The present invention is directed generally to disease management, and more particularly, to a computer system and method for the design, administration, and implementation of integrated disease management.

BACKGROUND

Disease management is a coordinated healthcare delivery program with the goal of improving overall health. As defined by the Disease Management Association of America, disease management is generally a system for coordinating healthcare interventions and communications for people having conditions in which patient self-care efforts are significant. A disease management program typically supports (1) the physician or other clinician/patient relationship and plan of care, (2) emphasizes prevention of disease exacerbations and complications utilizing treatment guidelines and patient empowerment strategies, and (3) evaluates clinical, humanistic, and economic outcomes on an on-going basis.

Many organizations offer disease management programs that provide telephonic contacts to patients diagnosed with a single disease, and provide supporting education materials to those patients. Diseases that have typically been focused on are: congestive heart failure, chronic obstructive pulmonary disease, asthma, diabetes and coronary artery disease (CAD). In general, disease management programs have several components which would typically include: population identification process; evidence-based practice guidelines; patient self-management education (including primary prevention, behavior modification programs, and compliance/surveillance); process and outcome measurement, evaluation, and management; and a routine reporting/feedback loop (including communication with patient, physician/clinician, health plan and ancillary providers, and practice profiling).

Traditionally implemented disease management programs have been telephonic based systems which implement these above mentioned components in successive phases. As an example, a model for implementing telephonic-delivered disease management programs could include a phase for identifying patients who may benefit from the program and creating a target list of those patients, another phase for contacting patients on the list by telephonic and other communication media, yet another phase for enrolling the contacted patient as a participant in the program, and finally a phase for executing patient intervention programs to achieve behavior change and subsequent improvement in outcomes. In a telephonic program, enrollment is based upon a case manager successfully recruiting patients to join the program over the phone.

In the first phase, traditional disease management programs identified patients on certain criteria, which included at least an analysis of the patient's prior claims and medical history. In these programs, the selection of patients to be contacted was done by a case manager or a computer system that would analyze certain data to determine eligibility without personal knowledge of the patient from prior relationship (i.e. there was no input from the patient's physician to confirm that the patient actually had a disease indicated by the patient's claim data or medical history or the like).

In the second phase of a traditional disease management program, after identifying the patients to be contacted, a case manager would cold call identified patients (i.e., contacts patients they do not know and have no prior relationship with) to recruit them into the disease management program. This contact made by a case manager was impersonal and not based on a relationship that otherwise exists between a patient and his/her trusted physician. Therefore, in traditionally implemented telephonic programs cold calling by a case manager suffers the additional inefficiency of not capitalizing of the relationship between the physician who knows the patient and his/her medical history (i.e. the trusted clinician) and the patient to successfully recruit patients to join the program over the phone.

In the third and fourth phases of the traditional disease management program, the contacted patients who agreed to join the disease management program underwent assessment and were enrolled in the program. Thereafter, a nurse coach would create and administer an individualized patient care plan. Traditionally, in these phases a patient's trusted clinician had no input or minimal input in the preparation and updating of the individualized patient care plan.

Theoretically, in a traditional disease management program, the cold calling in the second phase could result in the patient recognizing the need for care and opting to enroll into the disease management program associated with the case manager. In addition, theoretically, the lack of input from a patients trusted physician in the fourth phase may also be harmless in terms of the effectiveness of the care plan developed for the patient. In practice however, traditional disease management programs have not been entirely successful because, (i) the correct patients are not always identified due to discrepancies between a patient's actual condition and the diagnosis codes, (ii) only a small percentage of patients initially identified as potential participants join the program and even fewer continue to remain in the program, and (iii) a patient may end up following a care plan that is rigid and not personally tailored for his/her needs thereby reducing the chances that the patient will continue to stay with the program. For example, a patient's claim data may show a diagnosis code for diabetes making him/her an ideal candidate to be contacted by the case manager. In reality, however, the patient could simply have an incorrect code showing up in the report—a situation which a computerized system or a case manager not knowing the patient would not catch. As a result, this patient would be added to the target population to be contacted for enrollment, but would not be enrolled in the program because he/she did not have the disease suggested by the diagnosis codes. This failure to successfully target the correct patients leads to contact and enrollment inefficiencies. Similar inefficiencies result from the failure to recruit a diseased patient when the patient fails to enroll because he/she is contacted by a stranger who is not his usual or trusted clinician. Other inefficiencies also result from the failure to include the trusted clinician's knowledge of a patient's medical history to prepare a care plan for the enrolled patient.

These inefficiencies and failures are evidenced in traditional disease management programs. Although there is some variation in the efficiency levels at each of the four phases of a traditional disease management program on a vendor and program basis, an industry estimate is a 50% success rate at each phase. Starting with 100% at the beginning of phase 1; 50% of the target patient population is successfully contacted by the completion of phase 2; at the end of phase 3, 50% of contacted patients agree to become program participants by enrolling (also called opt-in); and at the end of phase 4, 50% of enrolled participants exhibit measurable behavior change, which ultimately drives improvement in disease outcomes. Thus, the cumulative efficiency, or engagement rate, at the completion of the target patient identification, contact (outreach), and enrollment phases is 25%, or, one out of four patients on the target list enroll in the program. At the final phase this model would expect only 12.5% of the originally targeted patients to actually exhibit behavior change.

Therefore, there is a need for a disease management program that overcomes the inefficiencies of the traditional disease management program and improves the measurable outcomes of a target population by improving the effectiveness of the intervention. There is a further need for a disease management program that leverages the relationship between the patient and a trusted physician/clinician to improve the effectiveness of a disease management program.

SUMMARY

It is an object of the present invention to provide an integrated disease management program that incorporates active participation of a patient's trusted clinician in (i) identifying patients who may benefit from the program by reviewing a patient's claim data for eligibility, (ii) contacting patients on the list in person, by telephonic or other communication media to explain the benefits of participating in a disease management program, and (iii) executing patient intervention programs to reduce the chances that the patient will opt-out of the program, thereby improving the efficiency of the traditional disease management program.

It is yet another object of the present invention to provide an integrated disease management program that creates a higher quality list of target patients by combining the use of a predictive modeling algorithm with the review of identified target patients' claim data and medical history by the patient's trusted clinician, to create the final target population.

It is still another object of the present invention to provide an integrated disease management program which incorporates the patient's trusted clinician in the contact phase to improve patient enrollment rates.

These and other objects of the invention may be accomplished by any known means, including by individuals, one or more computer systems, communication systems, such as, phones, email or the like, or any combination thereof.

BRIEF DESCRIPTION OF THE DRAWINGS

Additional aspects, features, and advantages of the invention, both as to its structure and operation, will be understood and will become more readily apparent when the invention is considered in light of the following description made in conjunction with the accompanying drawings that illustrate certain non-limiting embodiments of the disclosure, wherein:

FIG. 4 is one exemplary embodiment of an individualized care plan.

FIG. 5 is a flow chart of an integrated disease management program depicting pre-enrollment and enrollment according to one exemplary embodiment of the invention.

FIG. 6 is a flow chart of an integrated disease management system depicting re-enrollment according to one exemplary embodiment of the invention.

DETAILED DESCRIPTION

Figure 1:
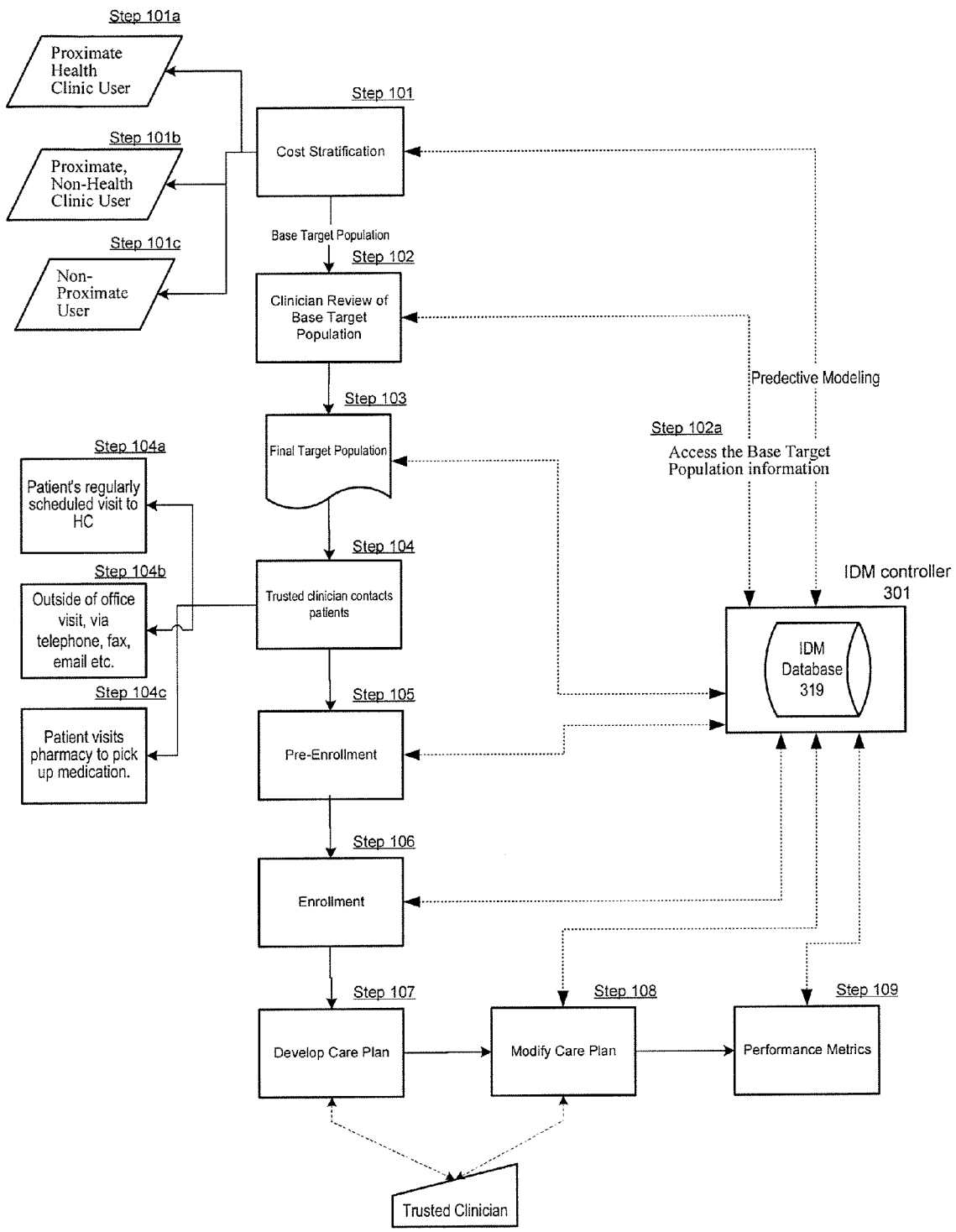
FIG. 1 is a flow chart of an integrated disease management program according to one embodiment of the invention.

The exemplary embodiments are discussed below with reference to on-site health clinics of a large, self-insured employer's active and retiree population along with their adult dependents. In the exemplary embodiments, the employer locations have an on-site primary care health clinic and a full-service pharmacy available to active and retired employees and their dependents. This exemplary embodiment is presented for convenience only and is not intended to limit the application of the present invention. After reading the following description, it will be understood by those skilled in the art how to implement the present invention in alternative embodiments involving patient care.

First Exemplary Embodiment

An exemplary embodiment of an integrated disease management (IDM) program is presented herein. In this example, the integrated disease management program is a flexible, network-based application that can be used to implement a disease management program through the process outlined in FIG. 1. As implemented in this embodiment, FIG. 1 outlines a methodology that integrates disease management with a work-site based trusted clinician who, for example, is a primary care physician, primary care nurse, pharmacist or a clinical staff member at the on-site health clinic office, to form an integrated disease management program.

Identification and Contact

At step 101 of this exemplary embodiment the IDM program incorporates a predictive model to analyze a patient's medical and pharmacy claims data to identify those patients who have the highest potential for improving healthcare by managing certain diseases they will encounter in their lifetime, and consequently, to identify those patients with the highest future avoidable healthcare costs. As currently known in the art, predictive modeling in disease management is the process of forecasting healthcare use/expenditure, which may be based on variables such as, (1) claims data, which contain information on patient age, gender, diagnoses, prescriptions, observed utilization and treatments, (2) clinical data, such as, lab results to forecast healthcare expenditures, and (3) data related to prior utilization and compliance with prescription regimens and plan design elements for prediction purposes. Predictive modeling based on this information can be carried out by any known means including, for example, using commercially available software applications sold by software vendors, such as, DxCG, Inc., Active Health Management, Inc., Symmetry and Accordant Health Services, Inc.

In this exemplary embodiment, at this step, claims data are analyzed using a predictive model to identify patients with at least one disease that is covered by the IDM program, and to determine the improvements that can be achieved in the patient's overall health along with the amount of avoidable overall health costs for the patient. As used in this embodiment, avoidable cost is that portion of the costs a patient is expected to incur that may be changed or avoided through some type of disease management intervention. This cost/health-benefit stratification in the predictive modeling (step 101) may be done by an application that is used to implement the IDM program discussed in FIG. 3 below.

Predictive modeling may be entity specific, and therefore, at this step, the criteria for a cost/health-benefit stratification may be based on any individual requirements for each self-insured employer implementing the integrated disease management program. By way of example, the cost/health-benefit stratification in the modeling may involve the following steps. First, the population of employees, retirees and dependents age 18 and older who are eligible for health benefits are identified. Next, for the patients within the identified eligible population, primary diagnosis codes from their individual medical claims (based upon International Statistical Classification of Diseases and Related Health Problems) are used to identify patients with recorded diagnosis codes, such as the diagnosis codes for diabetes, coronary artery disease or essential hypertension, that are covered under a disease management program. Data for this group of eligible patients, with a condition covered by a disease management program, is included in the predictive model which determines the avoidable costs for each identified patient and the corresponding predicted future health benefits for each patient. By way of example, the predictive model will forecast individual patient's total and avoidable healthcare costs for a forward-looking twelve (12) month period. By prioritizing patient targeting and enrollment processes based on members with high avoidable healthcare costs, the enrolled population will be enriched with patients who have actionable conditions (improved efficiency) amenable to the benefits of integrated disease management. By applying integrated disease management programs to this enriched population, program effectiveness is increased as measured by improved outcomes. This cost/health-benefit stratification in these embodiments may be done by an application that is used to implement the IDM program, which is discussed in FIG. 3 below.

In an alternative embodiment, each patient's proximity to the on-site health clinic may also be used as an additional factor in identifying patients. For example, patient's whose residence is within a predetermined proximity radius, for example, a 35 mile radius, of the on-site health clinic may be considered to be geographically proximate and have access to the on-site health clinic for the medical care of their chronic condition. Such patients may further be classified either as 'health center users' (101*a*), for example, those patients who have used the on-site health clinic for an office visit, or as 'proximate non-users' (101*b*), for example, those patients who do not use the on-site health clinic for office visits. In another embodiment, proximate non-users may also include those patients who only use the on-site health clinic for acute care treatment rather than primary handling of their chronic condition. Patients living outside of the predetermined proximity radius may be classified as 'non proximate' (101*c*). The resulting patient population is then stratified on health-benefits and avoidable costs, and those with the potential for the most significant health improvement and, consequently, high avoidable costs are selected.

The result of step 101 is the identification of the base target population. The base target population is processed in step 102 and undergoes claim stratification. During this step, by way of example, a trusted clinician may access the base target population information via a user interface to the application that is used to implement the IDM program (step 102*a*). Clinician encounter data is accessed by the trusted clinician. In this exemplary embodiment, clinician encounter data will include, for example, administrative claim equivalent data, patient medical record information, administrative claims and health insurance eligibility data, or the like for the patients in the base target population. The trusted clinician in conjunction with the IDM controller (301) that is used to implement the IDM program can combine clinician encounter data with patient medical record information, administrative claims and health insurance eligibility data and identify appropriate patients within the base target population that should be enrolled in the employer's health center's disease management program. In an alternative embodiment, the IDM controller (301) processes clinician encounter data with patient medical record information, administrative claims and health insurance eligibility data and identify appropriate patients within the base target population that should be enrolled in the employer's health center's disease management program.

Steps 101 and 102, i.e. the stratification process, results in the selection of those patients with appropriate disease diagnoses for inclusion in a disease management program and the potential for the most significant improvement in health and reduction in healthcare costs. The review of the target population by the trusted clinician in step 102 refines the process of selecting appropriate candidates for inclusion in the disease management program. This is the final target population (103) (i.e., the group comprising the patients from the base target population who will benefit the most from participating in a disease management program).

In this exemplary embodiment, step 102 is an improvement over traditional methods because the trusted clinician (e.g., an entity that has a personal relationship with the patient and is treating the patient) can be used in identifying the target population, which in turn, allows the IDM program to improve the contact information data and clinical data of the base target population.

Figure 3:
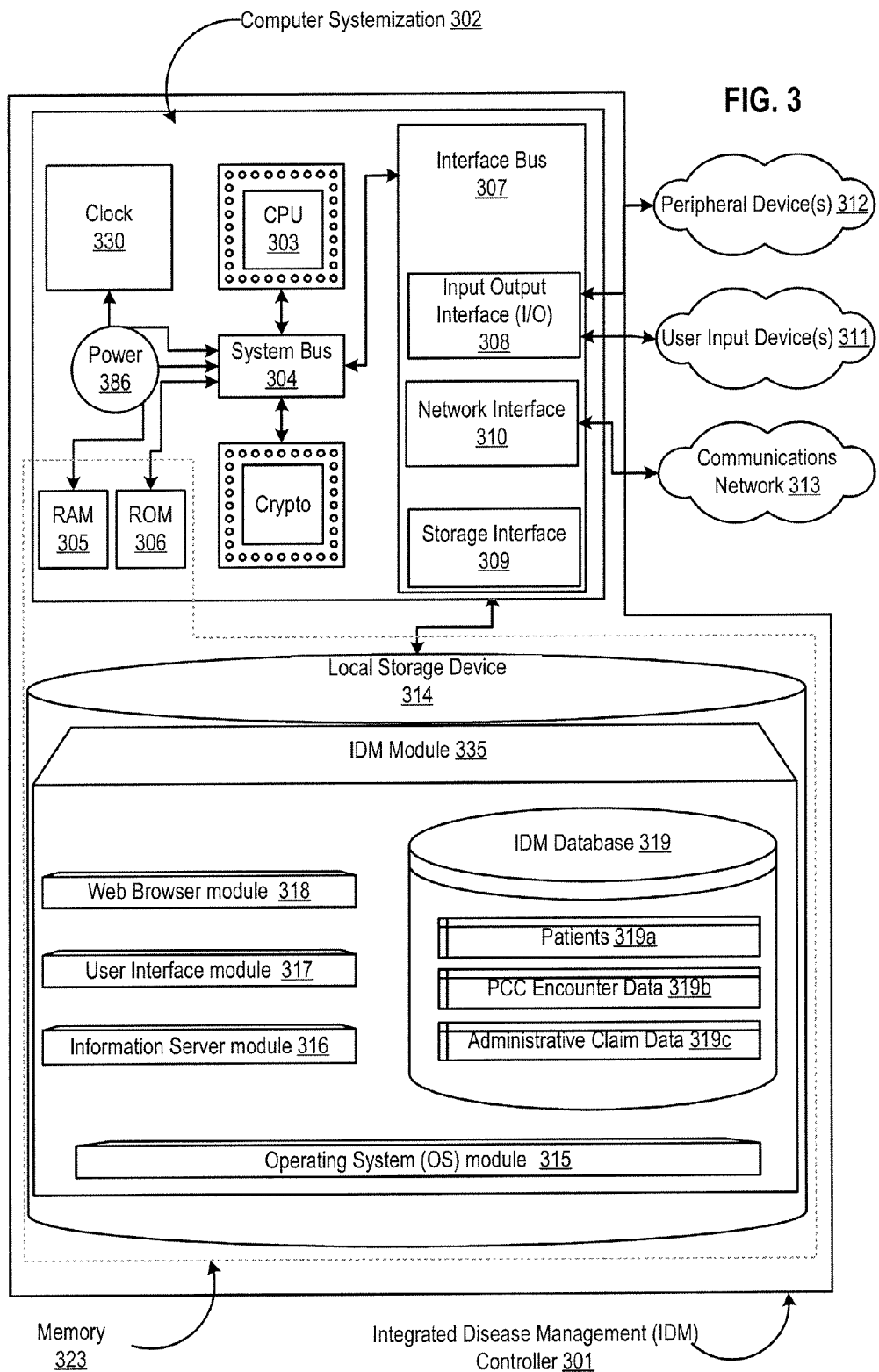
FIG. 3 is one exemplary embodiment of an integrated disease management program controller.

In step 103, the final target population list is generated. This list may be generated, for example, at a central facility which, in this embodiment is a network-based application that is used to implement the IDM program (FIG. 3). In this exemplary embodiment, the trusted clinician receives the patient list that is generated by the IDM controller (301) and saved on the IDM database (319). In other embodiments, this list may be generated using an automated tool similar to the IDM controller or manually, and the list may be sent to, and received by the trusted clinician using traditional fax or email services or the like.

Step 104 leverages the patient's relationship with a trusted primary care clinician or other on-site health clinic based trusted clinicians to contact and pre-enroll patients in a disease management program from the final target population. Using the trusted clinician to approach a patient about enrollment in the disease management program increases program effectiveness because, unlike traditional disease management systems, the IDM program seeks to engage both the patient and their trusted clinician to work together within the disease management framework. In step 104, the initial contact with the patient may be accomplished in several ways, for example, by telephonic, face-to-face, e-mail, web inquiry, etc. In one exemplary embodiment illustrated in FIG. 1, the trusted clinician initiates contact with the patient in at least one of the following ways: (i) the trusted clinician discusses the disease management program during the patient's regularly scheduled visit to the office (step 104*a*); (ii) the trusted clinician discusses the disease management program with the patient outside of an office visit, which by way of example, could be a telephone contact by the trusted clinician to the patient's home (step 104*b*); or (iii) the trusted clinician discusses the disease management program with the patient during his/her visit to the pharmacy to pick up prescribed medication (step 104*c*).

Thus as described above, the overall enrollment design in this exemplary embodiment is "opt-in;" i.e., once the final target population is identified, the patient is asked to consent to participate in the disease management program after an explanation of the program services, and they may "opt-out" or refuse to continue participation at any time.

Pre-Enrollment

As a result of step 104, once a patient in the final target population has been contacted, the trusted clinician attempts to pre-enroll the patient into a disease management program by educating the patient about the program and the potential health/cost benefit to the patient. As part of the pre-enrollment, the patient agrees to be contacted by a case manager. The patient's willingness to be contacted by a case manager of the disease management program (step 105) is captured in the patient's records, for example, in the IDM database (319) using the IDM controller (301), and is a successful pre-enrollment of the patient. In this exemplary embodiment, a case manager is the individual responsible for initially enrolling the patient, completing a general assessment, and scheduling a follow-up appointment with a nurse coach, who, for example, is a registered nurse providing care support and functions as a disease management nurse for patients.

The improved efficiency, in this phase of the IDM program, using the present method can be determined from the following equation:

$$\text{Patient contact rate} = \frac{\text{\# patient's successfully contacted}}{\text{\# patients in final target population}}$$

In this exemplary embodiment, successfully pre-enrolled patients are, by way of example, made accessible to a case manager while the patient is at the on-site health clinic or during a telephone conversation. If the patient does not have time while on-site to complete a general assessment (wellness and lifestyle assessment) with the case manager, the trusted clinician obtains a best day and time for contacting the patient, completes a referral/communication form, and faxes all information to the case manager. As a result of this step (105), an adjusted target population of patients is identified comprising the set of patients from the final target population who have been contacted by the trusted clinician and have consented to pre-enrollment. This group comprises a set of selected patients who will benefit from participating in a disease management program and have consented to complete the enrollment process in the disease management program. In an alternative embodiment, information about (1) the patient's general assessment with the case manager, (2) the best day and time for the nurse coach to contact the patient for a follow-up appointment, or (3) information on a referral/communication form is saved in the IDM database (319) using the IDM controller (301). It is to be noted that in a situation wherein all patients in the final target population agree to pre-enrollment, the group comprising the adjusted target population (i.e. patients who have agreed to be contacted by a case manager) is identical to the final target population.

Enrollment

In step 106, a case manager associated with the entity administering the disease management program contacts the patient and completes enrollment of the patient in the disease management program. By way of example, the enrollment process may include filling-out a questionnaire, a general assessment, providing educational material regarding the disease to be managed, and/or the like. As another example, the process of patient enrollment may be conducted on-line, via access to the IDM controller 301, where the enrollee would access the necessary forms to be filled-out and would also have access to educational and other material related to the disease and the disease management program. If, for example, the patient is contacted by the trusted clinician during his/her visit to the on-site health clinic (step 104*a*), then during the visit itself, a case manager may make the initial call to the patient while he/she is at the on-site health clinic, complete the general assessment and schedule a follow-up appointment with a nurse coach. This second contact step of enrolling the patient into the disease management program results in increased enrollment efficiency which is, for example, evident in the higher enrollment rate for patients exposed to the IDM program than for patients exposed to the traditional disease management program. At least one factor attributable to this increased enrollment efficiency is the unique approach of steps 101 and 102 of this exemplary embodiment of the IDM program and the corresponding success of the pre-enrollment step 102. The patient enrollment rate metric may be defined as:

$$\text{Patient enrollment rate} = \frac{\text{\# patient's enrolled}}{\text{\# patients successfully contacted (adjusted target population)}}$$

Once enrolled, in step 107, the patient receives an individualized care plan (FIG. 4), which represents an outline i.e. a blue-print of the IDM program for a particular patient. In this exemplary embodiment, the patient enrolled in the IDM program receives a care plan that tracks the patient's progress during their participation in the program. Office visit data and test results are recorded along with detail notes made by the nurse coach. This information may be gathered and updated, for example, by the IDM controller 301. In this exemplary embodiment, a nurse coach, who, for example, is a registered nurse, provides care support and functions as a disease management nurse for patients of the adjusted target population. A case manager is responsible for initially enrolling the patient, completing a general assessment, and scheduling the nurse coach follow-up appointment.

Step 108 is unique to the IDM program because once again, the patient's relationship with the trusted clinician again leveraged to modify the patient's individualized care plan to suit the patient. In this step, the three main entities of the IDM program, for example, the trusted clinician, the patient and the nurse coach discuss the issues, problems, required level of care, etc. and decide on a care plan that all entities are comfortable with and a plan that has a high rate of success. It is to be noted that this step may be different from a traditional disease management program wherein, for example, a nurse coach would make decisions with or without input from the trusted clinician. In this embodiment, however, the IDM program includes the trusted clinician in the decision making process to increase program effectiveness.

After step 108, the IDM program performance metrics are determined (step 109) to evaluate the effectiveness of the IDM program. By way of example, such performance metrics would involve the use of three metrics to evaluate enrollment effectiveness: (i) contact rate, i.e. the number of individuals successfully contacted divided by the number of individuals in the final target population, where a successful contact is talking with an individual, (ii) enrollment rate, i.e. the number of individuals enrolled into the program divided by the number of individuals successfully contacted (adjusted target population) where enrollment is securing an individuals agreement to participate in the program and completing an initial 15-20 minute assessment, and (iii) engagement rate, i.e. the weighted enrollment rate which is the product of the contact rate multiplied by the enrollment rate.

In alternative embodiments, additional metrics dealing with health outcomes and participant satisfaction can be combined with the enrollment effectiveness measures to evaluate the overall program effectiveness.

Second Exemplary Embodiment

Figure 2:
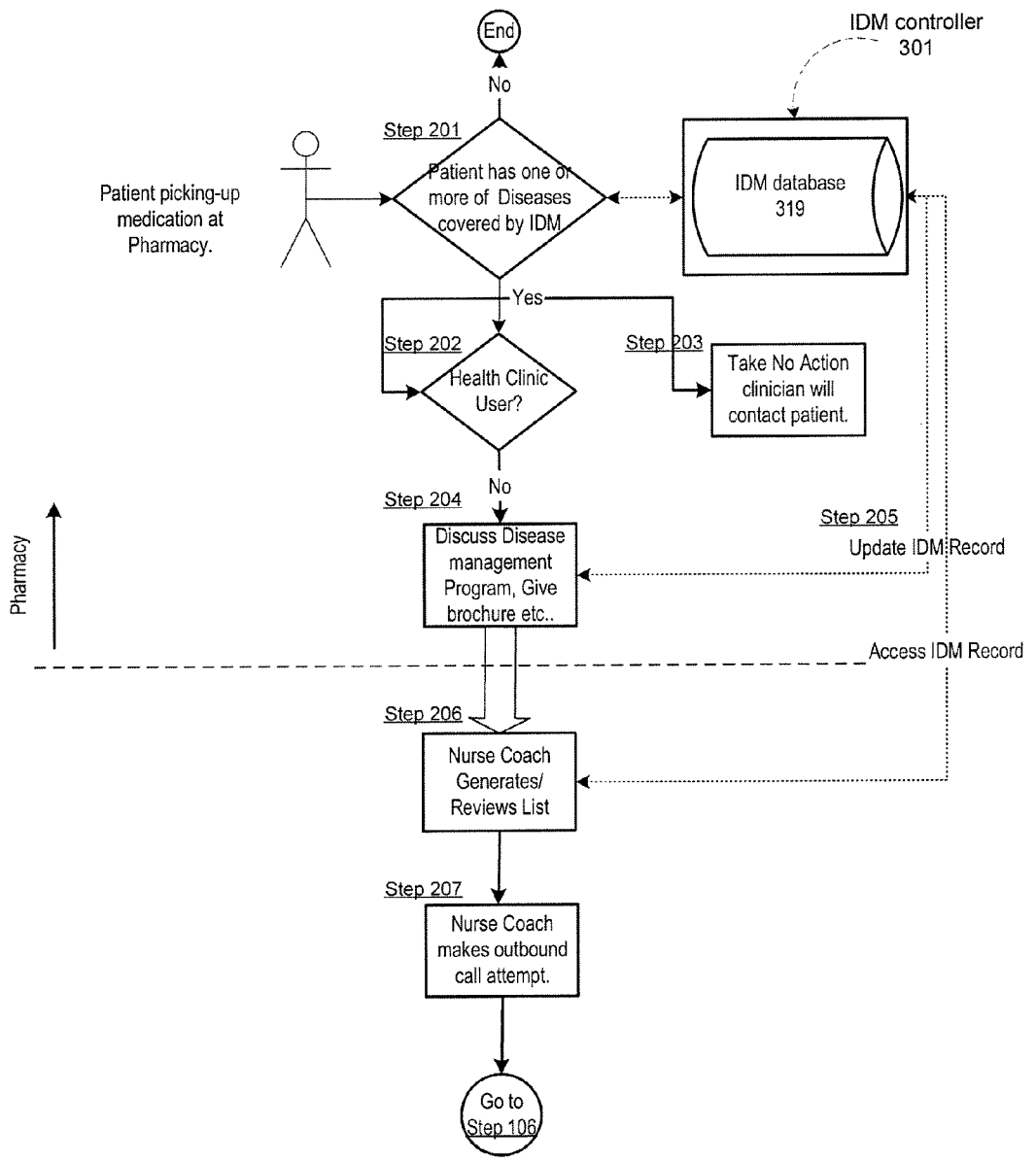
FIG. 2 is one exemplary embodiment of the integrated disease management program's pharmacy referral process.

A second exemplary embodiment of an integrated disease management program is presented herein. In this example, the integrated disease management program is a flexible, network-based application that can be used to implement a disease management program through a pharmacy referral process outlined in FIG. 2.

In this embodiment, at step 201, the patient attempts to get a prescription filled. The pharmacist (i.e. trusted clinician) checks the patient medication to see if he/she is being treated for any disease that is covered by the health center disease management program. If yes, then at step 202, the pharmacist accesses the patient information, for example, from the application used to implement the IDM program (FIG. 3). If a query to the IDM controller (301) determines that the patient is an on-site health clinic user, then no action is taken and the patient will be contacted/enrolled as described in the exemplary embodiment of FIG. 1 (step 203). If the patient is not an on-site health clinic user, then at step 204, the pharmacist discusses the disease management program with the patient and can, for example, give informative material regarding the disease and the program to the patient. Next, at step 205, the pharmacist updates the patients information in the IDM controller (301) and can also fax the referral to a case manager. At step 206, a case manager at the entity administering the disease management program generates a list of all patients with updated pharmacy records by, for example, accessing the IDM controller (301). In an alternative embodiment a case manager can also use a list that is faxed by the pharmacy to initiate the contact with the patients. At step 207, a case manager makes the outbound call attempt, and as detailed in the exemplary embodiment of FIG. 1, continues to perform steps similar to step 106-step 109.

Third Exemplary Embodiment

A third exemplary embodiment of an integrated disease management program is presented herein. In this example, the integrated disease management program is a flexible, network-based application that can be used to implement a disease management program through a pre-enrollment and enrollment process outlined in FIG. 5.

In this embodiment, after step 104 (FIG. 1), at step 501 the patient is introduced to the disease management program. If the patient agrees, he or she is pre-enrolled and the patient's record is updated in the IDM database (319) using the IDM controller (301). Alternatively, if the patient declines, the patient record is updated in the IDM database (319) using the IDM controller (301) (step 502). In this exemplary embodiment, the trusted clinician completes an on-line referral form by accessing the form via a remote connection to the IDM controller (301) (step 503). This referral form may be alternatively generated as a fax, email, secure message, phone call or other standard communication method. At step 504, in this exemplary embodiment, the control passes to a case manager, who accesses the IDM controller (301) to generate a list of patients that have pre-enrolled in the disease management program (i.e. the group of second selected patients). After accessing patient information, the case manager contacts the patients in this group. In this exemplary embodiment, the contact by a case manager may be, for example, an outbound contact call from the case manager to the patient within 1 business day of generating the list (step 505). If contact is made, and the patient agrees to the enrollment, the case manager completes a general assessment (step 506) and schedules an appointment with a nurse coach (step 507). If the patient declines, the on-site health clinic is notified and the patient record is updated (step 510) in the IDM controller (301). Once follow-up appointment with the nurse coach is complete and the patient is enrolled in the disease management program, the nurse coach updates the IDM database (319) using the IDM controller (301) for the patient. In this exemplary embodiment, in the event that no contact is made with the patient the nurse coach reschedules a general assessment to be completed the following week (step 508). In this regard, the nurse coach makes two attempts over the subsequent two weeks to contact the patient. If no contact is made, the nurse coach updates the IDM controller (301) and sends a no-contact postcard to the patient (step 509). If there is still no response, or if the patient declines, the nurse coach notifies the on-site health clinic of the same and updates the IDM database (319) using the IDM controller (301) for the patient (step 510). This notification to the on-site health clinic may be in the form of a report generated by the IDM controller (301), or alternatively, this notification may be in the form of a fax, email, secure message, phone call or other standard communication method.

Fourth Exemplary Embodiment

A fourth exemplary embodiment of an integrated disease management program is presented herein. In this example, the integrated disease management program is a flexible, network-based application that can be used to implement a disease management program through a re-enrollment process outlined in FIG. 6.

In this embodiment, for re-enrollment of a patient after non-enrollment verification of eligibility of the patient must be completed, which is conducted by a trusted clinician or a nurse coach in conjunction with the IDM controller (301), as discussed in FIG. 1. At step 601a-c, a list containing a population of patients who are eligible for re-enrollment is generated. By way of example, this list can be generated by any one or more of the following: (i) a nurse coach generates a list of re-enrollees, (ii) an on-site health clinic staff member contacts a nurse coach with a list of re-enrollees, or (iii) a patient calls in requesting enrollment in the disease management program. In this embodiment, only a nurse coach may re-enroll a member into the IDM program to ensure appropriate clinical assessment, for example, by making the outbound call to the patient. Steps 602a-c and 603a-c are conducted by the nurse coach. Next, at step 610 the nurse coach will need to obtain verification of eligibility of the patient by, for example, accessing the patient's records in the IDM database (319) using the IDM controller (301). In alternative embodiments, verification of eligibility can be done by contacting the on-site health clinic.

In steps 602a-c the nurse coach determines when the last contact was made. If 90 or more days have elapsed since last patient contact, then the nurse coach must complete general and disease specific assessment (step 603a) and, by way of example, the patient's answers are used by the IDM controller (301) to creates a customized care plan including suggested educational material, clinical outreach/referral, follow-up frequency etc. In alternative embodiments, these assessments are conducted annually and on an "adhoc" basis if there is a dramatic change in health status. If 60 days have elapsed since last patient contact, then the nurse coach must complete only the disease specific assessment (step 603b). If 30 days or less have elapsed since last patient contact, then the nurse coach must complete a disease specific follow-up assessment (step 603c). By way of example, a disease-specific follow-up assessment is a shortened version of the disease-specific assessment and is used as a guide by the nurse coach during monthly follow-up contacts. In this exemplary embodiment, such an assessment is a manual process and entered as a narrative note in the IDM controller (301), is not mandatory, but is used as a guide for the nurse coach to structure the interaction, if desired. At step 604, the IDM program determines if assessment is complete. If yes, and if the patient is a current on-site health clinic user, then the patient's record is updated (step 608) and the patient is re-enrolled (step 605). If assessment is complete and the patient is not a current on-site health clinic user, then the patient's record is created and, in this exemplary embodiment, the on-site health clinic is notified of the patient's desire to start using the health center (step 606). The trusted clinician then schedules an appointment with the patient and the patient is re-enrolled (step 607).

Integrated Disease Management Controller

FIG. 3 is of a block diagram illustrating one exemplary embodiment of aspects of an integrated disease management (IDM) controller 301 which can be used to implement the foregoing processes. In this exemplary embodiment, the IDM controller 301 in FIG. 3 is based on common computer systems that may comprise, but is not limited to, components such as a computer systemization 302 connected to memory 323.

A computer systemization 302 may comprise a clock 330, central processing unit (CPU) 303 which comprises at least one high-speed data processor adequate to execute program modules for executing user and/or system-generated requests, a read only memory (ROM) 306, a random access memory (RAM) 305, and/or an interface bus 307, and most frequently, although not necessarily, are all interconnected and/or communicating through a system bus 304. Optionally, the computer systemization may be connected to an internal power source 386 and any of the above components may be connected directly to one another, connected to the CPU, and/or organized in numerous variations employed as exemplified by various computer systems.

Generally, any mechanization and/or embodiment allowing a processor to affect the storage and/or retrieval of information is regarded as memory 323. It is to be understood that the IDM controller 301 and/or a computer systemization 302 may employ various forms of memory 323. In a typical configuration, memory 323 will include ROM 306, RAM 305, and a storage device 314. The memory 323 may also contain a collection of program and/or database modules and/or data such as, but not limited to: operating system module(s) 315, information server module(s) 316, user interface module(s) 317, Web browser module(s) 318, database(s) 319, IDM module(s) 335, and/or the like. These modules may be stored and accessed from the storage devices and/or from storage devices accessible through an interface bus. Although non-conventional software modules such as those in the module collection, typically, are stored in a local storage device 314, they may also be loaded and/or stored in memory such as: peripheral devices, RAM, remote storage facilities through a communications network, ROM, various forms of memory, and/or the like.

In this embodiment, the IDM controller 301 may be connected to and/or communicate with entities such as, but not limited to: one or more users from user input devices 311, peripheral devices 312, and/or a communications network 313. It should be noted that although user input devices and peripheral devices may be employed, the IDM controller may be embodied as an embedded, dedicated, and/or monitor-less (i.e., headless) device, wherein access would be provided over a network interface connection.

The IDM controller 301 serves to process, store, search, serve, identify, instruct, generate, match, and/or update information, expirations, and/or other related data, such as, for example, accessing the IDM database 319 via the IDM module(s) 335 of the memory 323 to retrieve patient information, transmitting the patient information to the case manager or on-site health clinic, updating patient information, storing individualized care plans. Typically, users, which may be people, for example, clinicians, nurse coach, health service representative, case manager, and/or other systems, engage information technology systems (e.g., commonly computers) to facilitate information processing.

An IDM database 319 may be embodied in a database and its stored data. The database may include stored program code, which is executed by the CPU; the stored program code portion configuring the CPU to process the stored data. In this embodiment, the IDM database 319 includes several tables, for example, 319*a-c*. A patients table 319*a* may include fields such as, but not limited to: a patient's name, address, patient_id; claim_id; diagnosis_id, contact_id, enrollment_id and/or the like. The patients table may support and/or track multiple entity accounts on a the IDM program. A clinician encounter data table 319*b* includes fields such as, but not limited to: encounter_id, admin_user_id (a user given administrative status to control the account), patient_id, and/or the like. For example, a patient's visit to his/her primary care specialist may have its unique encounter_id key field used as part of the patient's table as one way to track encounters per patient. An administrative claims data table 319*c* includes fields such as, but not limited to: claim_id; patient_id, encounter_id, diagnosis_code and/or the like. For example, a patient's visit to his/her primary care specialist may have its unique claim_id key field used as part of the patient's table as one way to track claims per patient.

The IDM database 319 may communicate to and/or with other modules in a module collection, including itself, and/or facilities of the like. Most frequently, the IDM database 319 communicates with an IDM module 335, other program modules, and/or the like. The database may contain, retain, and provide information regarding other nodes and data, and may also be replicated at time intervals.

IDM module(s) 335 is stored program code that is executed by the CPU. The IDM module affects accessing, obtaining and the provision of information, services, transactions, and/or the like across various communications networks. The IDM module 335 enables the selection of the target population for a disease management program and customization of the manner in which information about the program participants, such as patients, clinician, case manager etc., can be captured, processed and displayed via a web client interface. In this embodiment, the IDM controller 301 employs the web server and user interface modules to obtain user inputs to, for example, specify selection criteria for potential patients based on target population and clinician encounter data, patient information, administrative claims and health insurance eligibility data and generates, for example, final target population list. By way of example, one non-limiting exemplary embodiment for the deployment of an integrated disease management program is implemented as an application in accordance with an Internet protocol, such as the HTTP, Extensible Markup Language ("XML"), or HTML protocol.

The configuration of the IDM controller 301 will depend on the context of system deployment. Factors such as, but not limited to, the budget, capacity, location, and/or use of the underlying hardware resources may affect deployment requirements and configuration. Regardless of if the configuration results in more consolidated and/or integrated program modules, results in a more distributed series of program modules, and/or results in some combination between a consolidated and distributed configuration, data may be communicated, obtained, and/or provided.

Overview of the System Process

An exemplary embodiment of an integrated disease management (IDM) system process is presented herein. The IDM controller 301 manages the patient information and the predictive modeling algorithm for selecting patients based on cost/health-benefit and claim stratification. The IDM controller 301 receives a request to generate a list of eligible patients i.e. final target population, and transmits the list to the user i.e. trusted clinician. The trusted clinician accesses the list via a user interface on a remote terminal that is connected to a central facility i.e. the IDM controller 301. The trusted clinician can use the IDM controller 301 to generate the contact with a patient if, for example, the contact is made via e-mail or the like. Alternatively, as discussed hereinabove, the trusted clinician can contact the patient via a telephone. Once contacted, the patient's response to the contact is updated in the IDM controller 301. In this embodiment, for example, patient information is updated by using a user interface on a remote terminal that is connected to the IDM controller 301, and once saved, the IDM database 319 record for the patient is updated. As a result of these processes, the IDM controller 301 is able to identify those patients who are eligible for participating in a disease management program and have consented to participate in such a program after being contacted by a trusted clinician who has, at least, explained the program and its benefits to the patient.

Thereafter, the IDM controller 301 receives another request to generate a list of contacted patients i.e. the pre-enrolled patients and transmits the list to the user i.e. case manager. The case manager accesses the list via a user interface on a remote terminal that is connected to a central facility i.e. the IDM controller 301. The case manager can use the IDM controller 301 to generate the contact with a patient if, for example, the contact is made via e-mail or the like. Alternatively, as discussed hereinabove, the case manager can contact the patient via a telephone to complete a general assessment and enroll the patient in a particular intervention program. Once this contact is successfully made, the patient's response to the contact is updated in the IDM controller 301. In this embodiment, for example, patient information is updated by using a user interface on a remote terminal that is connected to the IDM controller 301, and once saved, the IDM database 319 record for the patient is updated. As a result of these processes, the IDM controller 301 is able to identify those patients who, since pre-enrolling, have enrolled in a program after being contacted by a case manager who has, at least, completed a general assessment of the patient and has scheduled a follow-up visit with a nurse coach. Once enrollment is complete, the nurse coach with input from the patient and clinician accesses the IDM controller 301 to develop an individualized care plan for a patient, which is saved in the IDM database 319.

The center of the process revolves around the storage and management of patient information, claim data, contact information and care plan information in the IDM database 319. During the various processes described above, patient and other data related to the patient and his/her care is retrieved and/or updated in the IDM database 319 as required.

The entirety of this disclosure shows by way of illustration various embodiments in which the claimed invention may be practiced. In describing embodiments of the invention, in some cases specific terminology has been used for the sake of clarity, however, the invention is not intended to be limited to and/or by the specific terms so selected, and it is to be understood that each specific term includes all technical equivalents which operate in a similar manner to accomplish a similar purpose. It should be noted that terms and or phraseology in this disclosure are not exhaustive in detail, and are not provided as definitive definitions. Rather, the terms are provided herein simply as an aid to the reader. The terms are not limiting of the disclosure and/or claims herein. The use of the terms may contemplate any of the broader, and/or multiple meanings found in common use, dictionaries, technical dictionaries, and/or in actual use in the technical arts, as well as any broadening made throughout this disclosure.

Also, the advantages and features of the disclosure are of a representative sample of embodiments only, and are not exhaustive and/or exclusive. They are presented only to assist in understanding and teach the claimed principles. It should be understood that they are not representative of all claimed inventions. As such, certain aspects of the disclosure have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and functional, logical, organizational, sequence, structural, temporal, and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of space and reducing repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the invention, and inapplicable to others. In addition, the disclosure includes other inventions not presently claimed. As such, it should be understood that aspects of the disclosure such as advantages, embodiments, examples, features, functional, logical, organizational, sequence, structural, temporal, topological, and/or other aspects are not to be considered limitations on the disclosure as defined by the claims or limitations on equivalents to the claims.

What is claimed is:

1. A method for coordinated healthcare delivery for use with a controller, said controller including a processor and a memory communicatively coupled to said processor and having instructions that are executable by said processor, said method comprising:

generating a base target population of patients by analyzing, using said processor, claim data of each of a plurality of patients to determine a subset of said plurality of patients who are expected to realize a higher benefit from enrolling in a coordinated healthcare delivery program than other patients of said plurality of patients, wherein said base target population of patients is said subset of said plurality of patients;

generating, by said processor, a list of one or more patients in said base target population of patients that have had a previous contact with a clinician;

providing, using said processor, said claim data of each patient in said list of one or more patients in said base target population of patients to said clinician;

receiving, using said processor, for each patient of said base target population of patients in said list of one or more patients, an indication from said clinician with whom said patient has had said previous contact as to whether said patient is an appropriate candidate for enrollment in said coordinated healthcare delivery program, wherein said clinician with whom said patient has had said previous contact provides said indication based on a review of said claim data of said patient;

generating, using said processor, a final target population of patients, wherein said final target population of patients is a subset of said base target population of patients, wherein each patient of said final target population of patients has been indicated, by said clinician with whom said patient has had said previous contact, to be an appropriate candidate for enrollment in said coordinated healthcare delivery program based on said review of said claim data of said patient;

contacting patients from said final target population of patients, wherein, for each patient, said contact is made by said clinician with whom said patient has had said previous contact;

providing an identification of an adjusted target population of patients to a case manager responsible for enrolling patients from said adjusted target population of patients in said coordinated healthcare delivery program, wherein said adjusted target population comprises each patient from said final target population of patients who has agreed, during said contact by said clinician with whom said patient has had said previous contact, to be contacted by said case manager for enrollment in said coordinated healthcare delivery program after said contact by said clinician;

contacting said patients from said adjusted target population of patients for enrollment in said coordinated healthcare delivery program, wherein, for each patient, said contact is made by said case manager after receiving said identification of said adjusted target population of patients;

enrolling at least one patient from said adjusted target population of patients in said coordinated healthcare delivery program, wherein said enrolling is performed by said case manager after receiving said identification of said adjusted target population of patients; and generating a care plan for each enrolled patient, wherein said care plan is developed based upon interaction between one or more of said enrolled patient, said clinician with whom said enrolled patient has had said previous contact, and a nurse coach.

2. The method of claim 1, wherein said clinician is part of an on-site health clinic or pharmacy.

3. The method of claim 1, further comprising transmitting a list of said final target population of patients by at least one of:
(i) a central facility to a remote terminal within a peer-to-peer network or any data communication network capable of transmitting and receiving data from said central facility to said remote terminal; or
(ii) an email, fax, secure message, phone call or other standard communication method.

4. The method of claim 1, wherein providing said identification of said adjusted target population of patients to said case manager comprises providing said identification by at least one of:
(i) a central facility to a remote terminal within a peer-to-peer network or any data communication network capable of transmitting and receiving data from said central facility to said remote terminal; or
(ii) an email, fax, secure message, phone call or other standard communication method.

5. The method of claim 1, wherein said case manager is at least one of a registered nurse, a health service representative or a coordinated healthcare delivery representative.

6. The method of claim 1, wherein each patient from said final target population of patients is contacted by at least one of:
(i) said clinician during said patient's visit to an on-site pharmacy to pick up prescribed medication; or
(ii) said clinician outside of said patient's visit to an on-site health clinic and via any one of an email, a fax, a secure message, a phone call or other standard communication method.

7. The method of claim 1, wherein said clinician is any one of a primary care physician, a registered nurse, a nurse's assistant, a pharmacist, a pharmacy assistant or any other work-site based clinician with whom said patient has a pre-existing medical relationship.

8. The method of claim 1, further comprising rendering individualized patient care to each of said enrolled patients from a list of said adjusted target population of patients in accordance with said generated care plan.

9. The method of claim 1, wherein patient information for each of a list of said final target population of patients and a list of said adjusted target population of patients is stored in a central facility that can be accessed from a remote terminal connected to said central facility via a network.

10. A method for coordinated healthcare delivery for use with a controller, said controller including a processor and a memory communicatively coupled to said processor and having instructions that are executable by said processor, said method comprising:

receiving, from said processor, an identification of a base target population of patients generated by said processor by using a predictive model on a population of patients who are eligible to enroll in a coordinated healthcare delivery program to determine, for each of said eligible patients: (i) an amount of health costs said patient is expected to incur that may be avoided by enrollment in said coordinated healthcare delivery program; and (ii) a prediction of future health benefits corresponding to said amount of health costs that said patient may avoid by enrolling in said coordinated healthcare delivery program, wherein said base target population of patients is a subset of said eligible population of patients who are expected to realize a higher benefit, based on said predictive modeling of said amount of health costs that may be avoided and said corresponding future health benefits, than other ones of said eligible patients;

receiving, from said processor, a list of one or more patients in said base target population of patients that have had a previous contact with a clinician;

providing an indication to said processor, for each patient in said list of one or more patients in said base target population of patients, as to whether said patient is an appropriate candidate for enrollment in said coordinated healthcare delivery program based on a review of claim data of said patient by a clinician;

receiving, from said processor, an identification of a final target population of patients, wherein said final target population of patients is a subset of said base target population of patients, wherein each patient of said final target population of patients is a patient who has been indicated to be an appropriate candidate for enrollment in said coordinated healthcare delivery program based on said review of said claim data of said patient by said clinician with whom said patient has said preexisting medical relationship;

contacting patients from said final target population of patients, wherein, for each patient, said contact is made by said clinician with whom said patient has said preexisting medical relationship;

receiving an identification of an adjusted target population of patients, wherein said adjusted target population comprises each patient from said final target population of patients who has agreed, during said contact by said clinician with whom said patient has said preexisting medical relationship, to enroll in said coordinated healthcare delivery program, and wherein said processor is used to determine which patients of said final target population of patients are included in said adjusted target population of patients; and rendering individualized patient care, to each patient enrolled in said coordinated healthcare delivery program, by said clinician with whom said enrolled patient has said preexisting medical relationship, wherein each enrolled patient is at least one of a member of said adjusted target population of patients transmitted to a case manager, a patient contacted for enrollment in said coordinated healthcare delivery program by a case manager who does not have a medical relationship with said patient prior to contacting said patient for said enrollment in said coordinated healthcare delivery program, or a patient enrolled in a coordinated healthcare delivery program, and wherein an individualized care plan for each of said enrolled patients is developed based upon interaction between said enrolled patient and at least one of said clinician with whom said enrolled patient has said preexisting medical relationship or a nurse coach.

11. The method of claim 10, wherein receiving, from said processor, said identification of said final target population of patients comprises receiving said identification by at least one of:

(i) a central facility to a remote terminal within a peer-to-peer network or any data communication network capable of transmitting and receiving data from said central facility to said remote terminal; or (ii) an email, fax, secure message, phone call or other standard communication method.

12. The method of claim 10, wherein receiving said identification of said adjusted target population of patients comprises receiving said identification by at least one of:

(i) a central facility to a remote terminal within a peer-to-peer network or any data communication network capable of transmitting and receiving data from said central facility to said remote terminal; or (ii) an email, fax, secure message, phone call or other standard communication method.

13. The method of claim 10, wherein each patient from said final target population of patients is contacted by at least one of:

(i) said clinician during said patient's visit to an on-site pharmacy to pick up prescribed medication; or (ii) said clinician outside of said patient's visit to an on-site health clinic and via any one of an email, a fax, a secure message, a phone call or other standard communication method.

14. The method of claim 10, wherein said clinician is any one of a primary care physician, a registered nurse, a nurse's assistant, a pharmacist, a pharmacy assistant or any other work-site based clinician.

15. The method of claim 1, further comprising:

generating a re-enrollment population of patients, wherein each patient in said re-enrollment population has at least one of a group of diseases requiring coordinated healthcare delivery, is eligible to enroll for coordinated healthcare delivery, and is eligible for re-enrollment in said coordinated healthcare delivery program;

transmitting a list of said re-enrollment population of patients to said nurse coach;

contacting said patients from said list of said re-enrollment population of patients, wherein said contact is made by said nurse coach;

completing assessment of each of at least one of said contacted patients; and re-enrolling at least one of said contacted patients in said coordinated healthcare delivery program.

16. The method of claim 15 wherein each of said patients eligible for re-enrollment in said coordinated healthcare delivery program is at least one of:

a patient who is currently not enrolled in said coordinated healthcare delivery program;

a patient of said final target population of patients who declined enrollment during said contact by said clinician with whom said patient has had said previous contact;

a patient of said adjusted target population of patients who declined enrollment during said contact by said case manager;

a patient who has contacted a health clinic or a clinician with whom said patient had a previous contact to enroll into said coordinated healthcare delivery program;

a patient who was previously enrolled in said coordinated healthcare delivery program which has since expired; or a patient who is a new employee or is newly diagnosed with at least one of said group of diseases.

17. A method for coordinated healthcare delivery for use with a controller, said controller including a processor and a memory communicatively coupled to said processor and having instructions that are executable by said processor, said method comprising:

identifying a population of patients who are eligible to enroll in a coordinated healthcare delivery program;

generating, using said processor, a base target population of patients from said eligible population of patients based on predictive modeling of at least one of improved health benefits or avoidable health costs, wherein said base target population of patients is a subset of said eligible population of patients;

generating, using said processor, a list of one or more patients in said base target population of patients that have had a previous contact with a clinician;

receiving, using said processor, for each patient of said base target population of patients in said list of one or more patients, an indication from said clinician with whom said patient has had a previous contact as to whether said patient is an appropriate candidate for enrollment in said coordinated healthcare delivery program, wherein said clinician with whom said patient has had said previous contact provides said indication based on a review of claim data of said patient;

generating, using said processor, a final target population of patients, wherein said final target population of patients is a subset of said base target population of patients, wherein each patient of said final target population of patients has been indicated, by said clinician with whom said patient has had said previous contact, to be an appropriate candidate for enrollment in said coordinated healthcare delivery program based on said review of said claim data of said patient;

contacting patients from said final target population of patients, wherein, for each patient, said contact is made by said clinician with whom said patient has had said previous contact;

providing an identification of an adjusted target population of patients to a case manager responsible for enrolling patients from said adjusted target population of patients in said coordinated healthcare delivery program, wherein said adjusted target population comprises each patient from said final target population of patients who has agreed, during said contact by said clinician with whom said patient has had said previous contact, to be contacted by said case manager for enrollment in said coordinated healthcare delivery program after said contact by said clinician;

contacting said patients from said adjusted target population of patients for enrollment in said coordinated healthcare delivery program, wherein, for each patient, said contact is made by said case manager after receiving said identification of said adjusted target population of patients;

enrolling at least one patient from said adjusted target population of patients in said coordinated healthcare delivery program, wherein said enrolling is performed by said case manager after receiving said identification of said adjusted target population of patients; and generating a care plan for each enrolled patient.

18. The method of claim 1, wherein said plurality of patients comprises an eligible population of patients selected from a group of patients having at least one of a group of diseases requiring coordinated healthcare delivery, wherein each eligible population patient is eligible to enroll for coordinated healthcare delivery, and wherein generating said base target population of patients is performed based on predictive modeling of at least one of improved health benefits or avoidable health costs.

19. The method of claim 10, wherein said eligible population of patients comprises patients selected from a group of patients having at least one of a group of diseases requiring coordinated healthcare delivery, and wherein each eligible population patient is eligible to enroll for coordinated healthcare delivery.

* * * * *